US009380778B2

(12) United States Patent
Huang et al.

(10) Patent No.: US 9,380,778 B2
(45) Date of Patent: Jul. 5, 2016

(54) ANTHROQUINONE CONTAINING DERIVATIVES AS BIOCHEMICAL AGRICULTURAL PRODUCTS

(75) Inventors: Huazhang Huang, Woodland, CA (US); Brian Campbell, Davis, CA (US)

(73) Assignee: Marrone Bio Innovations, Inc., Davis, CA (US)

( * ) Notice: Subject to any disclaimer, the term of this patent is extended or adjusted under 35 U.S.C. 154(b) by 130 days.

(21) Appl. No.: 12/897,776

(22) Filed: Oct. 4, 2010

(65) Prior Publication Data

US 2011/0082215 A1 Apr. 7, 2011

Related U.S. Application Data

(60) Provisional application No. 61/248,878, filed on Oct. 5, 2009.

(51) Int. Cl.
| A01N 35/02 | (2006.01) |
| A01P 3/00 | (2006.01) |
| A01N 35/06 | (2006.01) |
| A01N 65/00 | (2009.01) |
| A01N 65/08 | (2009.01) |
| A01N 65/20 | (2009.01) |
| A01N 65/30 | (2009.01) |
| A01N 65/42 | (2009.01) |

(52) U.S. Cl.
CPC .............. *A01N 35/06* (2013.01); *A01N 65/00* (2013.01); *A01N 65/08* (2013.01); *A01N 65/20* (2013.01); *A01N 65/30* (2013.01); *A01N 65/42* (2013.01)

(58) Field of Classification Search
CPC ....... A01N 35/06; A01N 65/08; A01N 65/20; A01N 65/30; A01N 65/42; A01N 65/00; A01N 25/30
USPC .......................................... 514/680; 552/208
See application file for complete search history.

(56) References Cited

U.S. PATENT DOCUMENTS

| 3,726,850 | A | | 4/1973 | Detroit |
| 3,813,236 | A | | 5/1974 | Allan |
| 3,929,453 | A | | 12/1975 | Dimitri |
| 4,381,194 | A | | 4/1983 | Delli Colli |
| 4,602,004 | A | * | 7/1986 | Cohen ........................... 514/23 |
| 4,612,051 | A | | 9/1986 | Miller |
| 4,666,522 | A | | 5/1987 | Hollis |
| 4,863,734 | A | | 9/1989 | Pommer |
| 5,300,521 | A | | 4/1994 | Eberle |
| 5,668,183 | A | | 9/1997 | Leuenberger |
| 5,885,604 | A | | 3/1999 | Ballinger |
| 5,989,429 | A | | 11/1999 | Bardinelli |
| 5,994,266 | A | | 11/1999 | Hobbs |
| 6,172,004 | B1 | | 1/2001 | Brinker |
| 7,344,730 | B1 | | 3/2008 | Stadler |
| 7,867,507 | B2 | | 1/2011 | Birthisel |
| 2003/0012804 | A1 | | 1/2003 | Cutler |
| 2004/0096428 | A1 | * | 5/2004 | Jijakli et al. ................. 424/93.5 |
| 2005/0163815 | A1 | | 7/2005 | Bowen |
| 2006/0247130 | A1 | | 11/2006 | van der Krieken |
| 2006/0257334 | A1 | * | 11/2006 | Dahms et al. ................... 424/59 |
| 2007/0191292 | A1 | | 8/2007 | Gandhi |
| 2007/0264363 | A1 | | 11/2007 | Bowen |
| 2008/0113920 | A1 | | 5/2008 | Yang |
| 2008/0193387 | A1 | * | 8/2008 | De Wolff ....................... 424/47 |
| 2009/0246293 | A1 | | 10/2009 | Ehr |
| 2010/0136132 | A1 | | 6/2010 | van der Krieken |
| 2010/0154498 | A1 | | 6/2010 | Valencia |
| 2010/0278890 | A1 | | 11/2010 | Winowiski |
| 2011/0015237 | A1 | | 1/2011 | Morita |
| 2011/0028500 | A1 | | 2/2011 | Su |
| 2012/0115728 | A1 | | 5/2012 | Su |
| 2012/0196751 | A1 | | 8/2012 | Namnath |

FOREIGN PATENT DOCUMENTS

| CN | 1387765 | | 1/2003 |
| CN | 1515152 | | 7/2004 |
| CN | 1961667 | | 5/2007 |
| DE | 4411895 | A1 * | 5/1995 |
| EP | 0173410 | | 3/1986 |
| JP | 08-099813 | A | 4/1996 |
| JP | 08-109112 | | 4/1996 |
| JP | 2000-033383 | | 2/2000 |

(Continued)

OTHER PUBLICATIONS

"Rheum palmatum and Rheum rhabarbarum". Internet Archive Date: May 19, 2000 [Retrieved from the Internet on: Mar. 9, 2012]. Retrieved from the Internet: http://web.archive.org/web/20000519232753/http://www.ansci.cornell.edu/plants/medicinal/rhub.html>.*
Federal Register, vol. 70 Issue 182 (Wednesday, Sep. 21, 2005).*
Xinfeng Zhang, Phuong Thien Thuong, WenYi Jin, Nguyen Duy Su, Dai Eun Sok, KiHwan Bae, and Sam Sik Kang, Antioxidant Activity of Anthraquinones and Flavonoids from Flower of Reynoutria sachalinensis, Arch Pharm Res vol. 28, No. 1, 22-27, 2005.*
McCutcheon's vol. 1: Emulsifiers & Detergents, North American Edition, 2002; excerpt provided.*

(Continued)

*Primary Examiner* — Sarah Pihonak
*Assistant Examiner* — Jason A Deck
(74) *Attorney, Agent, or Firm* — Ying-Horng Liu; Chainey P. Singleton; Marrone Bio Innovations

(57) ABSTRACT

Formulations containing anthraquinone derivatives with increased effectiveness as pesticides are provided. These formulations may comprise (a) a preparation comprising one or more anthraquinone derivatives having activity against plant pests; (b) one or more C2-C7 alcohols, or glycols or lactones; and (c) one or more surfactants selected from the group consisting of a sulfate, ethoxylated fatty acid esters wherein said alcohols and surfactants are present in amounts effective to stability said preparation. Also provided are methods of using these formulations as pesticides.

20 Claims, No Drawings

(56) References Cited

FOREIGN PATENT DOCUMENTS

| | | |
|---|---|---|
| JP | 2000-034202 A | 2/2000 |
| JP | 2000033383 | 2/2000 |
| JP | 2000034202 | 2/2000 |
| WO | WO 98/11782 A1 | 3/1998 |
| WO | JP 2000-033383 | 2/2000 |
| WO | WO 03-005816 | 1/2003 |
| WO | WO 2004-000014 | 12/2003 |
| WO | WO 2005-010315 | 2/2005 |
| WO | WO 2006-015865 | 2/2006 |
| WO | WO 2006-037632 | 4/2006 |
| WO | WO 2006-037633 | 4/2006 |
| WO | WO 2006-037634 | 4/2006 |
| WO | WO 2007094533 A1 * | 8/2007 |
| WO | WO 2010-040834 | 4/2010 |

OTHER PUBLICATIONS

Evonic Industries Additives for Pesticide Formulations; Apr. 2008.*
Written Opinion of the International Searching Authority from counterpart PCT Application No. PCT/US2010/051359 filed Oct. 4, 2010.
Examination Report, New Zealand Patent Appln. 599664, dated Nov. 29, 2012, corresponding to U.S. Appl. No. 12/897,776.
Izahi. "Emodin—A Secondary Metabolite with Multiple Ecological Functions in Higher Plants", New Phytologist 105:205-217. 2007.
Kong et al., "Inhibition of MAO A and B by some plant-derived alkaloids, phenols and anthraquinones", J Ethnopharmacology. 91:351-355. 2004.
Tiebre et al., "Hybridization and Sexual Reproduction in the Invasive Alien Fallopia (Polygonaceae) Complex in Belgium", Annals of Botany. 99: 193-203. 2007.
Vrchotova et al., "The Stilbene and Catechin Content of the Spring Sprouts of Reynoutria Species", Acta Chromatographica, 19: 21-28. 2007.
Agarwal, S. et al. "Antifungal activity of anthraquinone derivatives from Rheum emodi" J. Ethnopharmacol., 72: 43-46. 2000.
Bardin, M., et al. "Compatibility between biopesticides used to control grey mold, powdery mildew and whitefly on tomato." Biological Control 46: 476-483. 2008.
Bartlett, D. W., et al. "The strobilurin fungicides." Pest Management Science 58: 649-662. 2002.
Belanger, R. R. and Benyagoub, M. "Challenges and prospects for integrated control of powdery mildews in the greenhouse." Canadian Journal of Plant Pathology 19: 310-314. 1997.
Bokshi, A. I., et al. "A single application of Milsana followed by Bion assists in the control of powdery mildew in cucumber and helps overcome yield losses." Journal of Horticultural Science and Biotechnology 83: 701-706. 2008.
Braun, U., et al. The taxonomy of the powdery mildew fungi. In The powdery mildews: a comprehensive treatise. R. R. Belanger, W. R. Bushnell, A. J. Dik and T. L. W. Carver. Eds. St. Paul, MN, APS Press: 13-55. 2002.
Bravo Fungicide draft, 10-1000L Draft Label Text. Container—Apr. 2009.
Burpee, L. and R. Latin "Reassessment of fungicide synergism for control of dollar spot." Plant Disease 92: 601-606. 2008.
Captan, General Fact Sheet. National Pesticide Information Center, 2002.
Daayf, F., A. Schmitt, et al. "The effects of plant extracts of Reynoutria sachalinensis on powdery mildew development and leaf physiology of long English cucumber." Plant Disease 79: 577-580. 1995.
De Waard, M. A. "Synergism and antagonism in fungicide mixtures containing sterol demethylation inhibitors." Phytopathology 86: 1280-1283. 1996.
Dow AgroSciences Nova™ 40W Agricultural Fungicide—Material Safety Data Sheet—Mar. 2009.
Durrant, W. E. and Dong, X. "Systemic acquired resistance." Annual Review in Phytopathology 42: 185-209. 2004.
F&N Tests Report No. 55:25—publication date: 1999.
F&N Tests Report No. 55:353—publication date: 1999.
F&N Tests Report No. 56:V76—publication date: 2000.
F&N Tests Report No. 57:V086—publication date 2001.
F&N Tests Report No. 58:V024—publication date 2002.
F&N Tests Report No. 58:V082—publication date: 2002.
F&N Tests Report No. 59:SMF029—publication date: 2003.
F&N Tests Report No. 59:V004—publication date 2003.
F&N Tests Report No. 59:V089—publication date: 2003.
F&N Tests Report No. 59:V135—publication date: 2003.
F&N Tests Report No. 60:V137—publication date: 2004.
Fofana, B. et al. "Milsana®-induced resistance in powdery mildew-infected cucumber plants correlates with the induction of chalcone synthase and chalcone isomerase" Physiol. Molec. Plant Pathol., 61, 121-132. 2002.
Fongicide Elevate® 50 WDG—Aug. 2007 (French language document).
Fraaije, B., et al. Qol resistance development in populations of cereal pathogens in the UK. BCPC International Congress—Crop Science and Technology, Alton, Hants, UK, pp. 689-694. 2003.
Gisi, U. "Synergistic interactions of fungicides in mixtures." Phytopathology 86: 1273-1279. 1996.
Hafez, M. B., et al. "The side-effects of plant extracts and metabolites of Reynoutria sachalinensis (F. Schmidt) Nakai and conventional fungicides on the beneficial organism Trichogramma cacoeciae Marchal (Hym., Trichogrammatidae)." Journal of Applied Entomology 123: 363-368. 1999.
Holb, I. J. and Schnabel, G. "The benefits of combining elemental sulfur with a DMI fungicide to control Monilinia fructicola isolates resistant to propiconazole." Pest Management Science 64: 156-164. 2008.
Horst, R. K., et al. "Effect of sodium bicarbonate and oils on the control of powdery mildew and black spot on roses." Plant Disease 76: 247-251. 1992.
Hwang, S.F., et al. "Effect of seed treatment and root pathogens on seedling establishment and yield of alfalfa, birdfoot trefoil and sweetclover." Plant Pathology Journal 5:322-328. 2006.
International Preliminary Report on Patentability dated Feb. 9, 2012 for counterpart international application serial No. PCT/US2020/043612.
International Preliminary Report on Patentability dated Apr. 19, 2012 for counterpart PCT application serial No. PCT/US2020/051359.
International Search Report (partial search) and Invitation to Pay Fees for Additional Search dated May 2, 2011 in counterpart PCT Application No. PCT/US10/043612.
International Search Report and Written Opinion dated Jun. 24, 2011 from counterpart PCT application serial No. PCT/US2010/051359.
International Search Report dated Jun. 29, 2012 from counterpart PCT application serial No. PCT/US11/59197.
International Search Report dated May 24, 2012 from counterpart PCT application serial No. PCT/US12/23571.
James, W. C. "A manual assessment keys for plant diseases." Key Nos. 2.2 and 2.4. American Phytopathological Society. St. Paul, MN, 1971.
Karaoglanidis, G. S. and Karadimos, D. A. "Efficacy of strobilurins and mixtures with DMI fungicides in controlling powdery mildew in field-grown sugar beet." Crop Protection 25: 977-983. 2006.
Konstantinidou-Doltsinis, S., E. Markellou, et al. "Control of powdery mildew of grape in Greece using Sporodex L and Milsana." Journal of Plant Diseases and Protection 114: 256-262. 2007.
Krishnakumari, G. et al. "Antifeedant activity of quinones from Ventilago madaraspatana" Fitoterapia, 72: 671-675. 2001.
Kuc, J., "Development and future direction of induced systemic resistance in plants" Crop Protection, 19: 859-861. 2000.
Lehnof. "A Reynoutria sachalinensis based plant extract for preventive control of powdery mildew." Biofa. <http://www.abim.ch/fileadmin/documentsabim/presentations2007/session5/1_lehnof_abim_2007.pdf> esp. pp. 5, 7, 8, 11, 14, 15. 2007.
Limpel, L. E., et al. "Weed control by dimethyl tetrachloroterephthalate alone and in certain combinations." N.E. Weed Control Conference. 16: 48-53. 1962.
Liu, Y. et al. "Anthraquinones in Rheum palmatum and Rumex dentatus (Polygonaceae), and phorbol esters in Jatropha curcas (Euphorbiaceae) with molluscicidal activity against the schistosome

(56) References Cited

OTHER PUBLICATIONS vector snails Oncomelania, Biomphalaria and Bulinus" Tropical Medicine and International Health, 2: 179-188. 1997.
May, R. M. "Evolution of pesticide resistance." Nature 315: 12-13. 1985.
McGrath M. T. "Fungicide resistance in cucurbit powdery mildew: Experiences and challenges." Plant Disease 85: 236-245. 2001.
McGrath, M. T. "Occurrence of strobilurin resistance and impact on managing powdery mildew on cucurbits." Cornell University; Vegetable MD Online 2003.
McGrath, M. T. "Guidelines for managing cucurbit powdery mildew in 2006." Cornell University, Vegetable MD Online 2006.
Muravieva. "Meditsina." 1978. Russian original.
Muravieva. "Meditsina." 1978. English translation.
Nash, R. G. "Phytotoxic Interaction Studies—Techniques for Evaluation and Presentation of Results" Weed Science 29: 147-155. 1981.
Office Action (Non-Final Rejection) dated Mar. 15, 2012 for U.S. Appl. No. 12/845,883.
Office Action (Final Rejection) dated Oct. 18, 2012 for U.S. Appl. No. 12/845,883.
Penncozeb® 80 WP fungicide. Group M Fungicide—label and booklet 2008 (Pest Management Regulatory Agency label transcript service) Pesticide Alert, Strawberry News Bulletin—Cabrio for use on strawberries. 2003 (English and Spanish documents).
Pesticide Alert, Strawberry News Bulletin—Cabrio for use on strawberries. 2003 (English and Spanish documents).
Randoux, B. et al. "Inhibition of *Blumeria graminis* f. sp. tritici Germination and Partial Enhancement of Wheat Defenses by Milsana" Phytopathology 96: 1278-1286. 2006.
Regalia® Bioprotectant Concentrate—Label—May 2009.
Regalia® SC a powerful New Tool for Powdery Mildew. Downy Mildew and Gummy Stem Blight on Cucurbits—May 2009 (fact sheet 1).
Regalia® SC a Powerful New Tool for Powdery Mildew Control on Cucurbits—May 2009 (fact sheet 2).
Reuveni, M. "Improved control of powdery mildew (*Sphaerotheca pannosa*)of nectarines in Israel using strobilurin and polyoxin B fungicides; mixtures with sulfur; and early bloom applications." Crop Protection 20: 663-668. 2001.
Richer, D. "Synergism—a patent view." Pesticide Science 19: 309-315. 1987.
Ross, A. F. "Systemic acquired resistance induced by localized virus infections in plants" Virology 14: 340-358. 1961.
Samoucha, Y. and Cohen, Y. "Synergy between metalaxyl and mancozeb in controlling downy mildew in cucumbers." Phytopathology 74: 1434-1437. 1984.
Schmitt, A. "Induced responses by plant extracts from Reynoutria sachalinensis: a case study." Bull. IOBC/WPRS 25: 83-88. 2002.
Schmitt, A., Use of Reynoutria sachalinensis plant extracts, clay preparations and Brevibacillus brevis against fungal diseases of grape berries. Fordergemeinschaft Okologisher Obstbau e.V. (FOKO) and der Staatlichen Lehr- und Versuchsanstalt fur Wein- und Obstbau (LvWO) Weinsberg. 10th International conference on cultivation technique and phytopathological problems in organic fruit-growing and viticulture; presentations at the meeting from Feb. 4-7, 2002 Weinsberg, Germany, pp. 146-151. 2002.
Schmitt, A. and Seddon, B. Biocontrol of plant pathogens with microbial BCAs and plant extracts—advantages and disadvantages of single and combined use. Modern fungicides and antifungal compounds IV. Proceedings of the 14th International Reinhardsbrunn Symposium 2004, BCPC, Atlon, UK, pp. 205-225. 2005. (abstract only submitted).
Schnabel, G., et al. "Reduced sensitivity in Monilinia fructicola to propiconazole in Georgia and implcations for disease management" Plant Disease 88: 1000-1004. 2004.
Singh et al., "Antifungal anthraquinones from Saprosma fragrans." Bioorganic & Medical Chemistry Letters 16:4512-4514. 2006
Su, H., "Sporulation of Bremia lactucae affected by temperature, relative humidity, and wind in controlled conditions". Phytopathology 94:396-401. 2004.
Subash, C. et al. "Determination and locational variations in the quantity of hydroxyanthraquinones and their glycosides in rhizomes of Rheum emodi using high-performance liquid chromatography" J. Chromatography A, 1097: 59-65. 2005.
Tamokou, J. et al. "Antimicrobial activities of methanol extract and compounds from stem bark of Vismia rubescens" J. Ethnopharmacol, 124: 571-575. 2009.
Third-Party Observations against EP patent application No. 10805012.1.
Van Den Bosch, F. and Gilligan, C. A. "Models of fungicide resistance dynamics." Annual Review of Phytopathology 46: 123-147. 2008.
Van Loon, et al. "Systemic resistance induced by rhizosphere bacteria." Annual Review of Phytopathology 36: 453-483. 1998.
Vechet, L, et al. "A comparative study of the efficiency of several sources of induced resistance to powdery mildew (*Blumeria graminis* f. sp. tritici) in wheat under field conditions." Crop Protection 28: 151-154. 2009.
Walters, D., et al. "Induced resistance for plant disease control: maximizing the efficacy of resistance elicitors." Phytopathology 85: 1368-1373. 2005.
Werner et al. "Anthraquinone-based bird repellent for sunflower crops." Applied Animal Behaviour Science 129(2-4):162-169. 2011.
Wurms, K., et al. "Effects of Milsana and Benzothiadiazole on the ultrastructure of powdery mildew haustoria in cucumber." Phytopathology 89: 728-736. 1999.
Wyenandt, C. A., et al. "Fungicide resistance management guidelines for cucurbit downy and powdery mildew control in the mid-Atlantic and Northeast regions of the US." Phytopathology 99 (2009 APS Annual Meeting Abtsracts of Presentations): S144-S144. 2009.
Yang, X-J. et al. "Synergistic interaction of physcion and chrysophanol on plant powdery mildew" Pest Manag Sci 63: 511-515. 2007.
Supplementary European Search Report in EP App. No. 10805012.1 dated Dec. 13, 2013, 11 pages.
International Search Report and Written Opinion in counterpart PCT Application No. PCT/US10/43612, dated Jul. 29, 2010.
Vrchotová,, N. et al., "Allelopathic properties of knotweed rhizome extracts" Plant Soil Environ., 54, 2008 (7):301-303.

\* cited by examiner

US 9,380,778 B2

ANTHROQUINONE CONTAINING DERIVATIVES AS BIOCHEMICAL AGRICULTURAL PRODUCTS

TECHNICAL FIELD

Disclosed herein are compositions and methods for formulating preparations containing anthraquinone derivatives (e.g., physcion, emodin, chrysophanol, and ventiloquinone so on) as biopesticides.

BACKGROUND OF THE INVENTION

With the rapid spread of resistance of plant pathogen populations to synthetic fungicides and increased awareness of human to environmental pollution, an alternative means of control plant diseases is very necessary. The most effective means is to boost the plant defense mechanisms by induced plant resistance [L. C. van Loon, P. A. H. M. Bakker, and C. M. J. Pieterse, Systemic resistance induced by Rhizosphere bacteria, *Annu. Rev. Phytopathol.* 1998. 36:453-83] and/or systemic acquired resistance [W. E. Durrant and X. Dong, Systemic acquired resistance, *Annu. Rev. Phytopathol.*, 2004, 42:185-209]. Therefore, reducing and/or delaying the formation of pathogen resistance and protecting environments.

Induced resistance is a state of enhanced defensive capacity developed by a plant when appropriately stimulated [Kuc, J., Development and future direction of induced systemic resistance in plants, Crop Protection, 2000, 19, 859-861]. Induced plant resistance can be triggered by chemicals, non-pathogens, avirulent forms of pathogens. When induced resistance is systemic, it is commonly referred as systemic required resistance [L. C. van Loon, P. A. H. M. Bakker, and C. M. J. Pieterse, Systemic resistance induced by Rhizosphere bacteria, *Annu. Rev. Phytopathol.* 1998.36:453-83].

Anthraquinone derivatives such as rhein, emodin, aloe-emodin, parietin, physcion, emodin-glycoside, physcion-glycoside, chrysophanol and chrysophanol-glycoside as well belong to one family of chemicals which induce plant resistance to pathogens. Induced resistance of this class of chemicals was well studied by using MILSANA®, the commercial name given to the extract of giant knotweed (*Reynoutria sachainensis*) [B. Fofana, D. J. McNally, C. Labbe, R. Boulanger, N. Benhamou, A. Seguin, R. R. Belanger, MILSANA® (*Reynoutria sachalinensis* extract)-induced resistance in powdery mildew-infected cucumber plants correlates with the induction of chalcone synthase and chalcone isomerase, *Physiol. Molec. Plant Pathol.* 2002, 61, 121-132]. Physcion and emodin are the major bioactive anthraquinone derivatives in MILSANA® (*Reynoutria sachalinensis* extract) that is verified in our laboratory by bioassay-guided fractionation. Glycoside derivatives of physcion and emodin are the minor for the activity. Numerous other studies in the agricultural field have shown that many anthraquinone derivatives displayed strong bioactivities such as antifungal, antifeedant, antimicrobial, molluscicidal activity [S. K. Agarwal, S. S. Singh, S. Verma, S. Kumar, Antifungal activity of anthraquinone derivatives from *Rheum emodi, J. Ethnopharmacol.* 72 (2000) 43-46S; J. D. D. Tamokoua, M. F. Tala, H. K. Wabo, J. R. Kuiatea, P. Tane, Antimicrobial activities of methanol extract and compounds from stem bark of *Vismia rubescens, J. Ethnopharmacol,* 2009, in press; G. N. Krishnakumari, B. Bhuvaneswari, I. R. Swapna, Antifeedant activity of quinones from *Ventilago madaraspatana, Fitoterapia,* 72 (2001) 671-675; Y. Liu, F. Sporer, M. Wink, J. Jourdane, R. Henning, Y. L. Li and A. Ruppel, Anthraquinones in *Rheum palmatum* and *Rumex dentatus* (Polygonaceae), and phorbol esters in *Jatropha curcas* (Euphorbiaceae) with molluscicidal activity against the schistosome vector snails *Oncomelania, Biomphalaria* and *Bulinus, Tropical Medicine and International Health,* 1997, 2(2), 179-188]. Synergism also exists in the interaction of these compounds such as in the interaction between physcion and chrysophanol [X-J., Yang, L-J., Yang, S-N., Wang, D-Z., Yu, H-W., Ni, Synergistic interaction of physcion and chrysophanol on plant powdery mildew, *Pest Manag Sci* 63:511-515 (2007)].

To protect the environments, MILSANA® (*Reynoutria sachalinensis*), a product derived from *Reynoutria sachalinensis*, was formulated as a water-based Suspension Concentrate (SC), registered as a biochemical pesticide (U.S. Pat. No. 4,863,734 Process for combating fungi; U.S. Pat. No. 5,989,429, Processes for forming stabilized biochemical agricultural products). MILSANA® (*Reynoutria sachalinensis*) is a very effective product for the control of mildew. However, two of the major problems that prevent it as a good commercial pesticide product are industrial reproducibility and the instability of the formulation. Reproducibility of making such a formulation is poor in industry. Because many chemicals in the extracts such as chlorophylls and anthraquinone derivatives are hydrophobic compounds, these compounds can aggregate together to form bigger particles as time passes by. Multiple difficulties are associated with such large particles. They are difficult to dissolve in water. Additionally, effective concentration of active ingredients in the application solution is decreased, resulting in worse efficacy; the big particles also can stick to the spraying containers and it is difficult to wash away with water. The big particles can even block the nozzles.

BRIEF SUMMARY OF THE DISCLOSURE

Disclosed herein are formulations of anthraquinone derivatives as biochemical agricultural products for use against plant pests, particularly plant phytopathogens such as plant pathogenic bacteria, fungi, insects, nematodes and/or as a molluscicide, as well as the use of pre- and post-emergence herbicide against weeds. In a particular embodiment, the anthraquinone derivative(s) used in compositions and methods disclosed herein is (are) the major active ingredients or one of the major active ingredients.

In particular, provided is a formulation comprising (a) a preparation comprising one or more anthraquinone derivatives having activity against plant pests; (b) one or more C2-C7 aliphatic alcohols or glycols and lactones, (c) one or more surfactants selected from the group consisting of a sulfate, ethoxylated fatty acid esters and optionally at least one of an antifreeze or a carrier which may be used to modulate phytopathogenic infection in a plant. The formulation may be in the form of a liquid (concentrate or ready to use), emulsion or solid.

In a particular embodiment, the formulation comprises a preparation comprising one or more anthraquinone derivatives having activity against plant pests dissolved in hexanol and ethanol and further comprises sodium lauryl sulfate and calcium propionate. The anthraquinone derivative may be present in an amount of about 0.001% to 45%, hexanol may be present in the amount of about 0.1% to 10%, ethanol may be present in the amount of about 0.1% to 20%, sodium lauryl sulfate may be present in the amount of about 0.01% to 15%, and calcium propionate may be present in the amount of about 0.001% to 10%.

In yet another particular embodiment, the formulation comprises (a) a preparation comprising one or more anthraquinone derivatives having activity against plant pests;

(b) hexanol; (c) sodium lauryl sulfate; (d) 2-[2-[3,4-bis(2-methoxyethoxy)oxolan-2-yl]-2-(2-methoxyethoxy)ethoxy] ethyl hexadecanoate; (e) calcium propionate; (f) propylene glycol and (g) water and is optionally in the form of a microemulsion. The preparation of (a) may be present in an amount of about 0.001% to 45%, hexanol is present in the amount of about 0.1-10%, 2-[2-[3,4-bis(2-methoxyethoxy)oxolan-2-yl]-2-(2-methoxyethoxy)ethoxy]ethyl hexadecanoate is present in the amount of 0.1-35%, propylene glycol is present in the amount of about 1% to 8%, sodium lauryl sulfate is present in the amount of about 0.01% to 15% and calcium propionate is present in the amount of about 0.001% to 10%. The invention further provides an aqueous formulation comprising (a) a preparation comprising one or more anthraquinone derivatives having activity against plant pests; (b) one or more bases; (c) one or more water miscible co-solvents. The preparation of (a) may be present in an amount of about 0.01-45% by weight; the base is present in an amount of about 0.1-10%; the co-solvent is present in the amount of 0.1% to 30%.

In a particular embodiment, the formulation comprises said derivative, a glycol (e.g., propylene glycol), an organic acid (e.g., formic acid), a base (e.g., sodium hydroxide or sodium carbonate). The preparation may be present in an amount of about 0.01 to about 45% by weight; the base is present in an amount of about 0.1% to 5%; propylene glycol is present in the amount of about 0.1% to 8% and organic acid is present in the amount of about 0.1% to 5%.

In a particular embodiment, formulations include but are not limited to water-based formulations such as suspension concentration (SC), microemulsion (ME), nanoemulsion (NE), soluble liquid (SL), ready-to-use (RTU), emulsion in water (EW), microencapsulated or nano-encapsulated formulations. It also includes oil-based formulations such as emulsifiable concentrate (EC), and powder formulations such as water-soluble powder (WSP), water dispersible granules (WDG) or water dispersible tablets (WGT).

In yet another particular embodiment, the formulation further comprises an antimicrobial agent which may be a chemical pesticide and/or biopesticide.

Also provided are methods of using the formulations set forth hereinabove for modulating phytopathogenic infection (e.g., fungus or bacteria) in a plant comprising applying to the plant and/or seeds thereof and/or substrate used for growing said plant an amount of the formulations disclosed herein effective to modulate said phytopathogenic infection.

The use of (a) a preparation comprising one or more anthraquinone derivatives having activity against plant pests; (b) one or more C2-C7 aliphatic alcohols, or C2-C7 glycols or C2-C7 lactones and (c) one or more surfactants selected from the group consisting of a sulfate for the preparation of a formulation for use against plant pests or alternatively use of (a) a preparation comprising one or more anthraquinone derivatives having activity against plant pests; (b) one or more bases; (c) one or more water miscible co-solvents for the preparation of a formulation for use against plant pests is provided.

In a particular embodiment, provided are methods of using the formulations set forth hereinabove to modulate infestation of plant pests in soil by applying to the soil an amount of the formulations set forth hereinabove effective to modulate said plant pest infestation.

The formulations set forth above and disclosed herein can be used simultaneously with an anti-microbial agent such as a biopesticide or chemical pesticide in a tank mix or in a program (sequential application called rotation) with predetermined order and application interval during the growing season. Thus, also provided is a combination comprising the formulation set forth above and the anti-microbial agent.

Alternatively, the formulations set forth above may further comprise an anti-microbial agent. In a particular embodiment, the antimicrobial agent is present in the amount of about 0.001% to about 10% by weight.

Formulations and combinations comprising the ingredients set forth above as well as anti-microbial agents may also be used to modulate infestation of plant pests on plants and/or soil and modulating phytopathogeic, fungal and bacterial infection.

DETAILED DESCRIPTION OF THE INVENTION

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise. For example, "a fungus" also encompasses "fungi".

As defined herein, the term "modulate" is used to mean to alter the amount of phytopathogenic, bacterial or fungal infection, plant pest infestation or rate of spread of phytopathogenic bacterial or fungal infection or plant pest infestation.

Anthraquinone Derivatives

Anthraquinone derivatives include but are not limited to physicion, emodin, chrysophanol, ventiloquinone, emodin glycoside, chrysophanol glycoside, physcion glycoside, 3,4-dihydroxy-1-methoxy anthraquinone 2-carboxaldehyde, damnacanthal. These derivatives share a similar structure as follows:

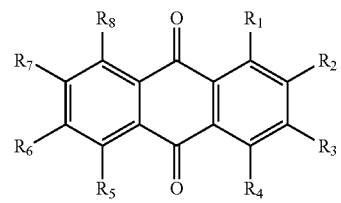

Where R1, R2, R3, R4, R5, R6, R7 and R8 are hydrogen, hydroxyl, hydroxylalkyl, halogen, carboxyl, alkyl, alkyoxyl, alkenyl, alkenyloxyl, alkynyl, alkynyloxyl, heterocyclyl, aromatic, or aryl group, sugars such as glucose.

In a particular embodiment, the invention is directed to anthraquinone derivatives that are contained in extracts derived from plant families including but not limited to Polygonaceae, Rhamnaceae, Fabaceae, Asphodelaceae, and Rubiaceae. These compounds can be isolated or obtained from any part of plants such as leaf, stem, bark, root and fruits. Plant materials can be wet and dry, but preferably dry plant materials. To meet the biochemical agricultural products, solvents and processes that are used in the extraction and purification must meet the requirements of National Organic Program (NOP) [www.ams.usda.gov/AMSv1.0/nop, cited on Jul. 20, 2009).

In a more particular embodiment, the plant extract is derived from a member of the Polygonaceae family. As defined herein, "derived from" means directly isolated or obtained from a particular source or alternatively having identifying characteristics of a substance or organism isolated or obtained from a particular source. In a particular embodiment, extract in said combination contains at least one anthraquinone derivative such as physcion and optionally emodin. Members of the Polygonaceae family include but are not limited to *Acetosella, Antigonon, Aristocapsa, Bilderdykia, Brunnichia, Centrostegia, Chorizanthe, Coccoloba, Coccolobis, Coccolobo, Corculum, Dedeckera, Delopyrum, Dentoceras, Dodecahema, Emex, Eriogonum, Fafopyrum, Fagopyrum, Fallopia, Gilmania, Goodmania, Harfordia, Hollisteria, Koenigia, Lastarriaea, Mucronea, Muehlenbeckia, Nemacaulis, Oxyria, Oxytheca, Perscarioa, Persicaria, Pleuropterus, Podopterus, Polygonella, Polygonum, Pterostegia, Rheum, Rumex, Ruprechtia, Stenogonum, Systenotheca, Thysanella, Tovara, Tracaulon, Triplaris* and even more particular embodiment, the extract may be derived from a *Reynoutria* (alternately referred to as *Fallopia*) sp or *Rheum* species. In a most particular embodiment, the extract is derived from *Reynoutria sachalinensis.*

In yet a more particular embodiment, percent concentration of anthraquinone derivatives in these formulations follows a range of between 0.001 to 99.99%. In a specific embodiment, the concentration range is between about 0.01 to 95%. The concentration is preferably between about 0.01% to about 45%.

Anthraquinone derivatives naturally exist in some plants, fungi, lichens, and insects. As noted above, in plants, they are present the different families such as Polygonaceae, Rhamnaceae, Fabaceae, Asphodelaceae, Rubiaceae and others [Subash C. Verma, Narendra P. Singh, Arun K. Sinha, Determination and locational variations in the quantity of hydroxyanthraquinones and their glycosides in rhizomes of *Rheum emodi* using high-performance liquid chromatography, *Journal of Chromatography A,* 1097 (2005) 59-65]. Anthraquinone derivatives widely distribute different plant tissues such as leaf, stem, bark, root and fruits. Physcion, as an example, exists in many herbs such as Chinese gooseberry (or Kiwi fruit, *Actinidia chinensis* Planch), abrus herb (*Abrus Cantoniensis* Hance), shan ma gen (*Boehmeria tricuspis* Hance), coffee senna seed (*Cassia occidentalis* L.), cassia seed (or seed of sickle senna *Cassia obtusifolia* L.), senna leaf (*Cassia angustifolia* Vahl.), leaf of ringworm senna (*Cassia alata* L.), common dysosmatis rhizome and Root (*Dysosma versipellis* Hance), bai ba jiao Tian (*Dysosma majorensis* Gagnep.), herb of tree clubmoss (*Lycopodium obscurum* L.), medicinal indian mulberry (*Morinda officinalis* How), root of thatch screwpine (*Pandanus tectorius* Soland), he shou wu (*Polygonum multiflorum* Thunb), ji xue qi (*Polygonum amplexicaule*), xue san qi (*Rheum likiangense* San.), xi zang suan mo (*Rumex patientia* L.), mao mai suan mo (*Rumexgmelini* Turcz.), niu she cao (*Rumex dentatus* L.), suan mo (*Rumex acetosa* L.), hu zhang (*Polygonum Cuspidatium*), to da huang (*Rumex obtusifolius* L.), to huang (*Rheum nodile* Hook.), yang ti (*Rumex japonicus* Houtt.), root of oriental buckthorn (*Rhamnus crenata* Sieb.), qian cao (*Rubia cordifolia* L.), da feng yao (*Rhamnus napelensis* Wall.), stem of sargentgloryvine (*Sargentodoxa cuneata* Oliv.), snow lotus herb (*Saussurea laniceps* Hand.) and so on [Chinese herb database www.tcmlib.com/ cited on Jul. 20, 2009].

Anthraquinone derivatives can be extracted from plant materials by any inorganic or organic solvents which are allowed to use by National Organic Programs [www.ams.usda.gov/AMSv1.0/nop, cited on Jul. 20, 2009]. For example, these materials can be ground and then extracted with a base solution, then acidified by an acid solution and finally extracted• by organic solvents such as ethyl acetate, butanol; or ground materials can be directly extracted with organic solvents such as ethanol, or ethyl acetate; or any other method and their combination to extract anthraquinone derivatives from plant materials. The extraction solution is then concentrated or dried under vacuum with an appropriate temperature such as 20-100° C., preferred to 30-70° C.

Formulations

Depending on extraction methods, extracts containing anthraquinone derivatives may include from very water soluble compounds (e.g., free sugars, glycosides, acids, amine acids and others) to very hydrophobic compounds (e.g., chlorophylls, Jong chain fatty acids, anthraquinone derivatives and others). The physical properties of these extracts may lead to problems for traditional oil-based formulations because hydrophilic compounds cannot dissolve in oil, but in water, and hydrophobic compounds cannot dissolve in water, but in oil. In addition, limited oils are allowed for organic farming [www.ams.usda.gov/AMSv1.0/nop, cited on Jul. 20, 2009]. Only extracts which was extracted with hydrophobic solvents such as ethyl acetate or butanol are suitable for oil-based formulations such as emulsifiable concentrate (EC). Therefore, powder and water-based formulations are the best choice for any extracts. Water-based formulations include suspension concentration (SC), microemulsion (ME), nanoemulsion (NE), soluble liquid (SL), emulsion in water (EW), ready-to-use (RTU) and microencapsulate or nano-encapsulate formulation. Powder formulations include but are not limited to water soluble powder (WSP), water dispersible granules (WDG) and water dispersible tablet (WGT). To easily compare with MIL-SANA® SC, dry ethanol extract powders of giant knotweed *Reynoutria sachalinensis* is used in all following formulation examples.

Suspension Concentrate

Suspension concentrate (also referred to as "SC") is defined as a stable suspension of solid particulate active ingredients in a liquid intended for dilution with water before use. The formulation may contain active ingredient, antifreeze, dispersant, stabilizer, water and others such as antimicrobial, antifoaming ingredients.

Physcion and emodin are the major technical active ingredients in dry ethanol extract powders of giant knotweed *Polygonum sachalinense.* Their melting points are over 200° C. and they are very stable in water. Therefore, based on active ingredients, knotweed ethanol extract is suitable for SC formulation.

Water-miscible organic solvents could help to dissolve some of hydrophobic compounds and solved problems about the aggregation or big particles. Basically, all water-miscible solvents from allowed substance lists in NOP [www.ams.usda.gov/AMSv1.0/nop, cited on Jul. 20, 2009] is possible unless phytotoxicity is shown at the highest recommended application rate. Such solvents include but are not limited to alcohols, which may include but are not limited to C2-C7 aliphatic alcohols (e.g., ethanol, isopropanol, glycols (e.g., propylene glycols), acids (e.g., acetic acid, propanoic acid) and lactones (e.g., gamma-butyrolactone). The maximal percent content of the watermiserable organic solvent in SC should allow maximal hydrophobic compounds to dissolve, but not produce phytotoxicity at the highest recommended application rate. The active ingredient in such a formulation follows a range of 0.001% to 90%, preferably 0.01% to 45%.

The preparation may be optimized by adjusting ethanol amount. Percent weight of ethanol was investigated at 1, 2, 4, 6, 8 and 10% in the final formulation. Based on physical properties of final formulations such as suspended particle size and precipitation, the formulation with 10% (W/W) ethanol was the best formulation.

Microemulsions

A microemulsion (also referred to as "ME") is a thermodynamic stable emulsion that is clear because the individual droplets of the dispersed phase are less than 100 nanometers in diameter. The composition of ME generally consists of active ingredients, antifreeze, co-solvent, surfactants, water and others such as antimicrobial agents. The active ingredient(s) for such a formulation is (are) within a range of 0.1-50%, preferably 1-30%.

Antimicrobial agents can prevent microorganisms from growing in the ME during storage. Any chemical listed in allowed substance in NOP [www.ams.usda.gov/AMSv1.0/nop, cited on Jul. 20, 2009] is suitable for such purpose. For example, bicarbonate salts, carbonate salts, propionate salt, sorbate salt, benzoate and so on. The amount of the antimicrobial agents follows a range of 0.1 to 15%, preferably 2-10%. The antimicrobial agent may be a chemical pesticide and in particular may a multi-site noninorganic, chemical fungicide selected from the group consisting of chloronitrile, quinoxaline, sulphamide, phosphonate, phosphite, dithiocarbamate, chloralkythios, phenylpyridin-amine, cyano-acetamide oxime. Alternatively, the chemical pesticide may be an insecticide or antibacterial agent that includes but is not limited to .carbamates, organophosphates, cyclodiene organochlorides, phenylpyrazoles, pyrethroids, pyret~rins, neonicotinoids, nitroguanadines, nicotine, Spinosyn, glycosides, juvenile hormone analogues and other insect growth regulators, pyridine azomethine, pyridine carboxamide, tetrazine, thiazolidinone, 2,4-diphenyloxzoline derivatives, organotin, pyrrole, buprofezin, hydramethylnon, naphtoquinon derivatives, pyridazinone, phenoxypyrazole, tetronic acid, carbazate, rotenone, organochlorinediphenylaliphatics. The antimicrobial agent may be a biopesticide derived from a microorganism such as *Streptomyces, Burkholderia, Trichoderma, Gliocladium* or may be a natural oil or oil-product having fungicidal and/or insecticidal activity (e.g., paraffin oil, tea tree oil, lemongrass oil).

Antifreezes are generally alcohols (e.g., isopropanol, butanol, glycerin or glycols such as propylene glycol), and sugars (e.g., glucose), which are listed in allowed substance in NOP [http://www.ams.usda.gov/AMSv1.0/nop, cited on Jul. 20, 2009]. However, antifreezes are not limited to these chemicals. Any chemical with low toxicity, especially natural chemicals, are suitable for this purpose. The percent content of antifreezes in ME depends on chemical properties, generally at a range of 0.1-15%, preferably at a range of 2-8%.

Co-solvents help to dissolve the active ingredients. They are generally alcohols including but not limited to C2-C7 aliphatic alcohols (e.g., ethanol, isopropanol, butanol, hexanol), ketones and esters (e.g., glyceryl triacetate, gamma-butyrolactone), which are listed in allowed substance in NOP [www.ams.usda.gov/AMSv1.0/nop, cited on Jul. 20, 2009]. However, co-solvents are not limited to these chemicals. Any chemical with low toxicity, especially natural chemicals, are suitable for this purpose. The percent content of co-solvents in ME depends on chemical properties, generally 0.1-20%, preferred to 1-15%.

A combination of surfactant would help to stabilize microemulsion. Generally, the combination includes a nonionic surfactant and an anionic surfactant or cation surfactant. Generally, hydrophile-lipophile-balance (HLB) of any surfactant combination listed in allowed substance in NOP [www.ams.usda.gov/AMSv1.0/nop, cited on Jul. 20, 2009] falls within 13 to 40 is suitable for this purpose. These surfactants, for example, include• but are not limited sulfate salt, phosphate salt, ethoxylated alcohols, ethoxylated fatty acid esters, ethoxylate phenols, ethoxylated fatty acids and so on. In a particular embodiment, the surfactant is at least one of 2-[2-[3,4-bis(2-methoxyethoxy)oxolan-2-yl]-2-(2-methoxyethoxy)ethoxy]ethyl hexadecanoate or sodium lauryl sulfate. The amount of the combined surfactants follows a range of 0.1-50%, preferably 10-40%.

Soluble Liquid or Soluble Concentrate

Soluble liquid (also referred to as "SL") (or soluble concentrate, also referred to as "SC") is a uniform liquid formulation. Active ingredient(s) is (are) dissolved in a liquid solvent (especially in water) with/without the aid of co-solvents and surfactants. The concentrate is then diluted with water when applied. Most of the anthraquinone derivatives (e.g., physcion, emodin, chrysophanol, ventiloquinone) used in the composition of the present invention possess one or multiple hydroxyl group on aromatic rings, which make the deprotonation easily under a basic condition. After forming salts, these anthraquinone derivatives would possess higher water solubility. Deprotonized anthraquinone derivatives such as emodin and physcion are still very active and they are stable in basic conditions. The content of the active ingredient (s) follows a range of about 0.001-80%, preferably 0.01-45%, more preferably about 0.02-25%.

The bases include but are not limited to carbonate salts (e.g., sodium carbonate, potassium carbonate etc), hydroxide salts (e.g., sodium hydroxide, potassium hydroxide and so on). Any allowed basic chemical allowed to use by NOP [www.ams.usda.gov/AMSv1.0/nop, cited on Jul. 20, 2009] that can deprotonate phenol hydroxyl group or form a salt with them will meets this purpose. The content of the base follows a range of about 0.1-10%, preferably about 0.2-5%.

Co-solvents for such a formulation are water miscible solvents such as alcohols (e.g., ethanol, isopropanol), acids (e.g., acetic acid, propanoic acid) and lactones (e.g., gammalactone). In a particular embodiment, it is a C2-C7 alcohol or glycol. Any water miscible solvents listed in NOP [www.ams.usda.gov/AMSv1.0/nop, cited on Jul. 20, 2009] are suitable for this purpose. The content of the co-solvent follows a range of about 0.1-20%, preferably about 0.1-15%.

Surfactants may be any dispersant allowed to use by NOP [www.ams.usda.gov/AMSv1.0/nop, cited on Jul. 20, 2009]. The dispersant includes but is not limited to humic acid, Vanisperse CB and so on. Surfactants for such a formulation can be those with high HLB values, generally over 12, preferably over 13. Any surfactants allowed to use by NOP [www.ams.usda.gov/AMSv1.0/nop, cited on Jul. 20, 2009] are suitable for such a purpose. These surfactants, for example, include but are not limited sulfate salt, phosphate salt, ethoxylated alcohols, ethoxylated fatty acid esters, ethoxylate phenols, ethoxylated fatty acids and so on. The amount of surfactants follows a range of 0.5-35%, preferably 3-8%.

Ready to Use (RTU)

Ready to use (also referred to as "RTU") is a formulation that is very low in concentration, used without dilution or mixing. It can be a solid (e.g., bait) or alternatively a liquid, frequently applied via a trigger sprayer bottle. Liquid RTU usually uses water as a carrier. RTU can be any one of the formulations such as ME, SL, SC and so on. The composition of such a formulation is similar to ME, SL or SC as described above.

Antimicrobial agents can prevent microorganisms from growing in the RTU during storage. Any chemical listed in allowed substance in NOP [www.ams.usda.gov/AMSv1.0/nop, cited on Jul. 20, 2009] is suitable for such purpose. For example, bicarbonate salts, carbonate salts, propionate salt, sorbate salt, benzoate and so on. The amount of the antimicrobial agents follows a range of 0.001 to 2%, preferably 0.01-0.5%. Stabilizers can be any chemical listed in allowed substance in NOP [www.ams.usda.gov/AMSv1.0/nop, cited on Jul. 20, 2009] that can stabilize anthraquinone derivatives in the water. It includes but is not limited to water miscible solvents such as ethanol, or inorganic salt such EDTA or any surfactants listed in allowed substance in NOP [www.ams.usda.gov/AMSv1.0/nop, cited on Jul. 20, 2009]. The amount of the stabilizer follows a range of about 0.001 to 2%, preferably about 0.01-0.1%.

Surfactants for such a formulation can be dispersants or any surfactant with high HLB values, generally over 12, preferably over 13. Any dispersant or surfactant allowed to use by NOP [www.ams.usda.gov/AMSv1.0/nop, cited on Jul. 20, 2009] are suitable for such a purpose. These surfactants, for example, include but are not limited sulfate salt, phosphate salt, ethoxylated alcohols, ethoxylated fatty acid esters, ethoxylate phenols, ethoxylated fatty acids and so on.) The amount of surfactants follows a range of 0.001-1%, preferably 0.01-0.5%.

Water Soluble Powder (WSP)

WSP is a powdered concentrate that can directly dissolve in water and result in spraying solution. Plant extracts containing anthraquinone derivatives may be formulated in a similar manner as with soluble liquid (SL) formulation except that solid carriers instead of water miscible co-solvent are used. Solid carriers are water soluble such as bicarbonate, carbonate and dextrins.

Water Dispersible Granules (WDG) and Water Dispersible Tablet (WGT)

These are the formulations that use carriers (e.g., kaolin, light calcium, white carbon black, silica soil algae) to absorb or stick the active ingredients, and use dispersants and other adjuvants to help disperse in water, resulting in spraying solution.

Emulsifiable Concentrate (EC)

This is a liquid concentrated form of pesticide that is mixed with water to create a spraying solution. When anthraquinone derivatives from plants are extracted with hydrophobic solvents listed in allowed substance by NOP [http://www.ams.usda.gov/AMSv1.0/nop, cited on Jul. 20, 2009], the extracts can be formulated as EC. Hydrophobic solvents include but are not limited to butanol, hexanol and ethyl acetate as well.

EXAMPLES

The examples below are presented to describe preferred embodiments and utilities of the invention and is not meant to limit the invention unless otherwise stated in the claims appended hereto.

Example 1

Soluble Concentrate

Preparation of 5% *Reynoutria sachalinensis* SC Product (Hereinafter Referred to as "5% MBI SC Product":

A) 50 gram of dry knotweed (*Reynoutria sachalinensis*) ethanol extract is homogenized in 100 gram of denatured ethanol at 600 rpm for at least 5 min; B) 378 gram of calcium nitrate is homogenized in 463 grams water for at least 5 min at 600 rpm; C) A and B are combined and then the mixture is homogenized at 2500 rpm for at least 5 min. At the end, the temperature of final formulation was about 44-50° C.

Evaluation of Physical Properties of 5% *Reynoutria sachalinensis* SC:

Dispersion and stability of new 5% SC was evaluated at 200-fold dilution with standard hard water (note: 200-fold dilution is recommended application rate). There was negligible insoluble precipitate (<1% of the total dry solid). Storage test at 4° C. and 54° C. for 2 weeks showed that there was a small layer of precipitates under the bottle, but this layer would be suspended again by slightly shaking the bottle. However, unlike the 5% *Reynoutria sachalinensis* SC, prepared using procedures described in U.S. Pat. No. 5,989,429 and marketed as MILSANA® from KHH there was no aggregation and no big particles observed. There was no nozzle blockage when applied with 5% MBI SC product.

Cucumber Powdery Mildew Bioassay:

The cucumber plants were 2-week old when treated. The first true open leaf was actively growing in all plants. MILSANA® from KHH at 200-fold dilution was used as a positive control. Five different batches of 5% MBI product marketed as REGALIA® SC samples were evaluated at 200-fold dilution. Treatments were prepared in water containing 0.02% (v/v) Nu-Film P. Treatments were applied using a 2 oz mist sprayer. Each plant was treated 3.5-4 ml (2.5-3 ml for upper side and 1 ml for lower side). Three hours after treatment, all plants were inoculated with a fresh conidial suspension of approximately $8.4 \times 10^5$ conidia per ml suspended in water. The number of powdery mildew lesions was determined 7 days after treatment/inoculation.

Comparison of Bioassay Results:

Results (Table 1) indicated that average efficacy of 5% MBI SC product SC was much higher than that of 5% MILSANA® SC. In addition, efficacy of 5% MBI SC product SC was reproducible through batch to batch.

TABLE 1

Comparison of efficacy between 5% Milsana ® SC and 5% Regalia ® SC toward cucumber powdery mildew *Sphaerotheca fuliginea*

| Treatments | Colony/leaf* | Control (%) |
|---|---|---|
| Untreated control | 196.0 ± 47.2 | 0 |
| MILSANA ® SC | 33.0 ± 11.7 | 83.2 |
| MBI SC product sample 1 | 7.3 ± 4.3 | 96.3 |
| MBI SC product sample 2 | 7.3 ± 1.1 | 96.3 |
| MBI SC product sample 3 | 5.5 ± 2.9 | 97.2 |
| MBI SC product sample 4 | 4.0 ± 2.1 | 98.0 |
| MBI SC product sample 5 | 1.0 ± 0.7 | 99.5 |

Example 2

Microemulsion (Hereinafter Referred to as "ME")

Preparation of 5% *Reynoutria sachalinensis* ME (Hereinafter Referred to as 5% MBI ME Product):

1) 5 gram of dry knotweed (*Reynoutria sachalinensis*) ethanol extracts are mixed with 2 gram hexanol and 2 gram propylene glycol at 900 rpm for 5 minutes; 2) 22 gram of 2-[2-[3,4-bis(2-methoxyethoxy)oxolan-2-yl]-2-(2-methoxyethoxy)ethoxy]ethylhexadecanoate and 3 gram sodium lauryl sulfate are added to the mixture and mixed at 900 rpm for 5 minutes; 3) 3 gram of calcium propionate is mixed with 63 gram of water; 4) The mixture from the step 3 is added to the mixture from step 2 by stirring at 900 rpm for 10 minutes to form a clear formulations. This formulation meets the dispersion and stability test, and also passed 2-week storage stability test at both 4 and 54° C.

Preparation of 20% *Reynoutria sachalinensis* ME (Hereinafter Referred to as 20% MBI ME Product):

1) 20 gram of dry knotweed (*Reynoutria sachalinensis*) ethanol extract is mixed with 7 gram hexanol and 4 grams propylene glycol at 900 rpm for 5 minutes; 2) 30 gram of 2-[2-[3,4-bis(2-methoxyethoxy)oxolan-2-yl]-2-(2-methoxyethoxy)ethoxy]ethyl hexadecanoate and 6 gram sodium lauryl sulfate is added to the mixture and all of the ingredients are mixed at 900 rpm for 5 minutes; 3) 6 gram of potassium sorbate is mixed with 27 gram of water; 4) the mixture from the step 3 is added into the mixture from the step 2 by stirring at 900 rpm for 10 minutes to form a clear formulation. This formulation meets the dispersion and stability test, and also passed 2-week storage stability test at both 4 and 54° C.

Cucumber Powdery Mildew Bioassay:

The Bioassay was performed as described above except that plants were inoculated with a conidial suspension of $2.4 \times 10^5$ conidia per ml. Two batches of 5% MBI ME Product was diluted at 200, 800 and 3200 times. One batch of 20% MBI ME Product was tested at 2000 fold dilution.

Comparison of Bioassay Results:

Results (Table 2) indicated that average efficacy of 5% MBI ME Product at 800 fold dilution was equal to or better than that of 5% MILSANA® SC at 200-fold dilution. Similarly, average efficacy of 20% MBI ME Product at 2000 fold dilution (Table 3) was equal to or better than that of 5% MILSANA® SC at 200-fold dilution.

TABLE 2

Comparison of efficacy between 5% MILSANA ® SC, 5% MBI ME Product toward cucumber powdery mildew *Sphaerotheca fuliginea*

| Treatment | dilution | Lesions | % control |
|---|---|---|---|
| Control | — | 381.7 | 0 |
| 5% MILSANA ® SC | 200 | 98.3 | 74.2 |
| 5% MBI ME Product (I) | 200 | 14.0 | 95.8 |
| 5% MBI ME Product (I) | 800 | 56.7 | 83.5 |
| 5% MBI ME Product (I) | 3200 | 280.0 | 32.7 |
| 5% MBI ME Product (II) | 200 | 7.7 | 97.9 |
| 5% MBI ME Product (II) | 800 | 83.3 | 78.4 |
| 5% MBI ME Product (II) | 3200 | 210.0 | 43.9 |

TABLE 3

Comparison of efficacy between 5% MILSANA ® SC, 20% MBI ME Product toward cucumber powdery mildew *Sphaerotheca fuliginea*

| Treatment | dilution | Average lesions | % control |
|---|---|---|---|
| Control | — | 388.0 | 0 |
| 5% MILSANA ® SC | 200 | 12.0 | 96.6 |
| 20% MBI ME Product | 2000 | 8.3 | 97.4 |

Example 3

Soluble Liquid (SL)

Preparation of 20% MBI SL Product:

1) 2 gram sodium hydroxide (or 5 gram sodium carbonate) is dissolved into 50 grams of water with 4 gram of propylene glycol; 2) 5 gram of liquid formic acids is added to dissolve; 3) 20 gram of dry knotweed (*Reynoutria sachalinensis*) ethanol extracts is added slowly with stirring at 900 rpm until a uniform solution is obtained. This formulation meets the dispersion and stability test, and also passed 2-week storage stability test at both 4 and 54° C. The pH value of such a formulation is around 8-8.5.

Cucumber Powdery Mildew Bioassay:

Bioassay was performed as described above except that plants were inoculated with a conidial suspension of $5 \times 10^5$ conidia per ml. Four batches of 20% MBI SL Product was diluted at 2000 times.

Comparison of Bioassay Results:

Results (Table 4) indicated that average efficacy of 20% MBI SL Product at 2000 fold dilution was equal to or better than that of 5% Milsana® SC at 200-fold dilution.

TABLE 4

Comparison of efficacy between 5% MILSANA ® SC, 20% MBI SL Product toward cucumber powdery mildew *Sphaerotheca fuliginea*

| Treatment | Dilution | Average lesions | % Control |
|---|---|---|---|
| Control | — | 388.0 | 0 |
| 5% MILSANA ® SC | 200 | 12.0 | 96.6 |
| 20% MBI SL Product (I) | 2000 | 0.3 | 99.9 |
| 20% MBI SL Product II) | 2000 | 0.7 | 99.8 |
| 20% MBI SL Product (III) | 2000 | 1.0 | 99.7 |
| 20% MBI SL Product (IV) | 2000 | 2.0 | 99.4 |

Example 4

Ready to Use (RTU)

Preparation of 0.025% MBI RTU-01 Product:

1) 0.25 gram dry knotweed (*Reynoutria sachalinensis*) ethanol extract is dissolved in 0.2 gram hexanol and 100 gram ethanol; 2) 0.3 gram of sodium laureth sulfate is added to the mixture, and mixed in; 3) 899.25 gram water is added to the mixture; the mixture is stirred at 900 rpm till a uniform solution is obtained. This formulation passed 2-week storage stability test at 4 and 54° C. It also did not show any phytotoxicity on many flowers Preparation of 0.025% MBI RTU-02 Product:

1) 0.25 gram dry knotweed (*Reynoutria sachalinensis*) ethanol extract is dissolved in 0.2 gram hexanol and 0.2 gram ethanol; 2) 0.09 gram of sodium laureth sulfate is added to the mixture, and mixed in; 3) 998.96 gram water is added to the mixture and mixed in as well; and 4) 0.3 gram of calcium propionate is added and mixed well by stirring at 900 rpm till a uniform solution is obtained. This formulation passed 2-week storage stability test at 4 and 54° C. It also did not show any phytotoxicity on many flowers.

Cucumber Powdery Mildew Bioassay:

Bioassay was performed as described above except that plants were inoculated with a conidial suspension of $5 \times 10^5$ conidia per ml. The same volume of 0.025% MBI RTU product was sprayed for each pot of cucumber plants as 200-fold dilution of 5% MBI ME product.

Comparison of Bioassay Results:

Results (Table 5) indicated that average efficacy of 0.025% MBI RTU product was equal to that of 5% MILSANA® ME at 200-fold dilution.

TABLE 5

Comparison of efficacy between 5% REGALIA ® ME and 0.025% REGALIA ® RTU toward cucumber powdery mildew *Sphaerotheca fuliginea*

| Treatment | Dilution | Severity % | % Control |
|---|---|---|---|
| Control | — | 92.5 ± 2.9 | 0 |
| 5% MBI ME Product | 200 | 0.5 ± 0.6 | 99.5 |
| 0.025% MBI RTU Product (I) | 1 | 0.0 ± 0.0 | 100 |
| 0.025% MBI RTU Product (II) | 1 | 2.5 ± 2.9 | 97.3 |

Although this invention has been described with reference to specific embodiments, the details thereof are not to be construed as limiting, as it is obvious that one can use various equivalents, changes and modifications and still are within the scope of the present invention.

Various references are cited throughout this specification, each of which is incorporated herein by reference in its entirety.

What is claimed is:

1. A formulation comprising
(a) a preparation comprising 0.01% to 45% by weight of a root extract derived from a root of *Reynoutria sachalinensis*, wherein said root extract comprises physcion, chrysophanol, and emodin in amounts effective to induce plant resistance to phytopathogens;
(b) 0.1% to 15% anti-microbial agent; and
(c) 0.1% to 50% by weight of one or more surfactants selected from a sulfate and ethoxylated fatty acid ester to stabilize said preparation.

2. The formulation according to claim 1, wherein said anti-microbial agent is 2% to 10% by weight and said surfactant is 0.01% to 15% by weight sodium lauryl sulfate, 0.1% to 35% by weight 2-[2-[3,4-bis(2-methoxyethoxy)oxolan-2-yl]-2-(2-methoxyethoxy)ethoxy]ethyl hexadecanoate or both.

3. The formulation according to claim 1, further comprising an alcohol or diol comprising 2-7 carbons wherein said alcohol or diol is selected from ethanol, isopropanol, butanol, hexanol, ethylene glycol and propylene glycol.

4. The formulation according to claim 1, further comprising 0.1% to 8% by weight propylene glycol.

5. The formulation according to claim 1, wherein
said root extract is 1% to 30% by weight;
said anti-microbial agent is 2% to 10% by weight;
said surfactant is 0.01% to 15% by weight sodium lauryl sulfate; and
10% to 40% by weight 2-[2-[3,4-bis(2-methoxyethoxy)oxolan-2-yl]-2-(2-methoxyethoxy)ethoxy]ethyl hexadecanoate.

6. The formulation of claim 1, further comprising at least one of (i) an antifreeze, (ii) a carrier or (iii) an antimicrobial agent having at least one of: fungicidal or insecticidal activity.

7. The formulation of claim 1, further comprising 2% to 10% by weight of an antimicrobial agent and 1% to 8% by weight of an anti-freeze selected from propylene glycol.

8. The formulation of claim 1, wherein the surfactant is 2-[2-[3,4-bis(2-methoxyethoxy)oxolan-2-yl]-2-(2-methoxyethoxy)ethoxy]ethyl hexadecanoate and sodium lauryl sulfate.

9. The formulation of claim 1, wherein the formulation is a liquid formulation.

10. The formulation of claim 1, wherein said preparation comprises
1% to 30% by weight said root extract of *Reynoutria sachalinensis;*
said one or more surfactants are 0.01% to 15% by weight sodium lauryl sulfate and 0.1% to 35% by weight 2-[2-[3,4-bis(2-methoxyethoxy)oxolan-2-yl]-2-(2-methoxyethoxy)ethoxy]ethyl hexadecanoate; and
said anti-microbial agent is 2% to 10% by weight; and further comprises 1% to 8% by weight propylene glycol.

11. The formulation of claim 1, wherein the formulation is a micro emulsion.

12. The formulation of claim 11,
further comprising hexanol in the amount of 0.1% to 10% by weight.

13. The formulation of claim 1, further comprising an anti-freeze agent in an amount of 2% to 8% by weight.

14. A formulation comprising:
a preparation comprising 1% to 30% by weight of a root extract derived from a root of *Reynoutria sachalinensis* that induces a plant resistance to powdery mildew, wherein said plant root extract comprises physcion, chrysophanol, and emodin;
0.1% to 15% by weight of an antifreeze having 2 to 7 carbons;
0.1% to 15% by weight of sorbate salt; and
10% to 40% by weight of one or more surfactants in amounts effective to stabilize said preparation selected from a sulfate and ethoxylated fatty acid ester.

15. The formulation of claim 14, wherein said antifreeze is propylene glycol.

16. The formulation of claim 15, further comprising an antifoaming agent, a carrier and an antimicrobial agent wherein said antimicrobial agent is selected from the group consisting of a chemical pesticide, biopesticide or natural or oil-product having fungicidal activity.

17. A formulation that induces a plant resistance to phytopathogens comprising
a preparation comprising
1% to 30% by weight of a root extract comprising physcion, chrysophanol, and emodin that induces a plant resistance to phytopathogens derived from a root of *Reynoutria sachalinensis;*
0.1% to 8% by weight of propylene glycol;
0.1% to 15% by weight of sorbate salt;
0.01% to 15% by weight sodium lauryl sulfate;
0.1% to 35% by weight 2-[2-[3,4-bis(2-methoxyethoxy)oxolan-2-yl]-2-(2-methoxyethoxy)ethoxy]ethyl hexadecanoate; and
an antifoaming agent; and
disposed in a carrier.

18. The formulation of claim 17, further comprising an antimicrobial agent wherein said antimicrobial agent is selected from the group consisting of a chemical pesticide, biopesticide or natural or oil-product having fungicidal activity.

19. A formulation comprising
(a) a preparation comprising 0.01% to 45% by weight of a root extract derived from *Reynoutria sachalinensis*, wherein said root extract comprises physcion, chrysophanol, and emodin in amounts effective to induce plant resistance to phytopathogens; and
(b) 0.1% to 50% by weight of one or more surfactants selected from a sulfate and ethoxylated fatty acid ester to stabilize said preparation.

20. A method for reducing a fungal infection in a plant comprising the steps of:
   providing a plant having a fungal infection, wherein the fungal infection is powdery mildew;
   applying the formulation of claim 1 to the plant in an amount effective to reduce said fungal infection.

\* \* \* \* \*